(12) United States Patent
Haraga et al.

(10) Patent No.: US 9,918,738 B2
(45) Date of Patent: Mar. 20, 2018

(54) ULTRASOUND-GUIDED PUNCTURE ASSIST DEVICE AND ULTRASOUND-GUIDED PUNCTURE METHOD USING THE SAME

(71) Applicant: Fukuoka University, Fukuoka (JP)

(72) Inventors: Isao Haraga, Fukuoka (JP); Kazuo Higa, Fukuoka (JP); Keiichi Nitahara, Fukuoka (JP)

(73) Assignee: Fukuoka University, Fukuoka (JP)

( * ) Notice: Subject to any disclaimer, the term of this patent is extended or adjusted under 35 U.S.C. 154(b) by 289 days.

(21) Appl. No.: 14/780,250

(22) PCT Filed: Mar. 27, 2014

(86) PCT No.: PCT/JP2014/058740
§ 371 (c)(1),
(2) Date: Sep. 25, 2015

(87) PCT Pub. No.: WO2014/157450
PCT Pub. Date: Oct. 2, 2014

(65) Prior Publication Data
US 2016/0051279 A1   Feb. 25, 2016

(30) Foreign Application Priority Data

Mar. 29, 2013   (JP) .................................. 2013-071417

(51) Int. Cl.
*A61B 8/00* (2006.01)
*A61B 17/34* (2006.01)
(Continued)

(52) U.S. Cl.
CPC ........ *A61B 17/3403* (2013.01); *A61B 8/0841* (2013.01); *A61B 8/4444* (2013.01);
(Continued)

(58) Field of Classification Search
CPC ................ A61B 8/0841; A61B 8/4444; A61B 2017/3413; A61B 2017/306; A61B 8/42; A61B 8/0891
See application file for complete search history.

(56) References Cited

U.S. PATENT DOCUMENTS

| | | | |
|---|---|---|---|
| 5,415,160 A | 5/1995 | Ortiz | |
| 2008/0006551 A1* | 1/2008 | Tolley | ................ A61B 17/3403 206/365 |
| 2012/0123461 A1 | 5/2012 | Pollak | |

FOREIGN PATENT DOCUMENTS

| | | |
|---|---|---|
| JP | 5337127 A2 | 12/1993 |
| JP | 7313516 A2 | 12/1995 |
| JP | 11206778 A2 | 8/1999 |

OTHER PUBLICATIONS

Shido, Akemi., "Utrasound-Guided Peripheral Nerve Blocks for Upper Abdominal Surgery—Where We Are and where We Will Be—," The Journal of Japan Society for Clinical Anesthesia, vol. 30, No. 7, 2010, pp. 959-966 and its English abstract.
(Continued)

*Primary Examiner* — Joel Lamprecht
(74) *Attorney, Agent, or Firm* — Rankin, Hill & Clark LLP

(57) ABSTRACT

[Problem]
Provided are: an ultrasound-guided puncture assist device that is capable of preventing occurrence of operational mistakes or the like when a nerve block or vascular puncture is performed under ultrasonography, an ultrasound-guided puncture method using the ultrasound-guided puncture assist device, and the like.
[Solution]
An ultrasound-guided puncture assist device with an object of preventing narrowing or the like of a puncture target site for a nerve block or vascular puncture under ultrasonogra-
(Continued)

phy to thereby assist the puncture by comprising a pulling mechanism for pulling the surface of the puncture target site, such as skin. The use of the ultrasound-guided puncture assist device of the invention can increase the width of the target site tissue where a nerve block or vascular puncture is performed, and thus occurrence of mispuncture is preventable.

3 Claims, 4 Drawing Sheets

(51) Int. Cl.
   *A61B 8/08* (2006.01)
   *A61B 17/00* (2006.01)
   *A61B 17/30* (2006.01)

(52) U.S. Cl.
   CPC ........ *A61B 17/3401* (2013.01); *A61B 8/0891* (2013.01); *A61B 8/42* (2013.01); *A61B 2017/00349* (2013.01); *A61B 2017/306* (2013.01); *A61B 2017/3413* (2013.01)

(56) References Cited

OTHER PUBLICATIONS

Fujiwara, Yoshihiro., and Kamatsu, Toru., Anesthesia 21 Century, vol. 9, No. 2-28, 2007, pp. 48-54.
International Search Report dated May 27, 2014 filed in PCT/JP2014/058740.

\* cited by examiner

ULTRASOUND-GUIDED PUNCTURE ASSIST DEVICE AND ULTRASOUND-GUIDED PUNCTURE METHOD USING THE SAME

TECHNICAL FIELD

The present invention relates to an ultrasound-guided puncture assist device, an ultrasound-guided puncture method using the same, and the like. More specifically, the present invention relates to an ultrasound-guided puncture assist device to be used in nerve block and vascular puncture, an ultrasound-guided puncture method using the same, and the like.

BACKGROUND ART

Nerve block is a therapeutic method for blocking pain signaling from a nerve(s) that is causing pain, which uses local anesthetic to be injected directly onto the nerve or into the neighboring tissue with needle or the like (Non Patent Literatures 1 and 2). For nerve block, injections are made in various areas including rectus sheath, transversalis fascia, and the like, and conventional approaches for nerve block include the landmark approach, electrical stimulation approach, and the like. In recent years, an approach in which nerve blocks are performed under ultrasonography is going mainstream.

Nerve blocks must be performed by specialist anesthesiologist because excellent technical skill is required to have injections made at target sites. However, even an anesthesiologist can make operational mistakes such as penetrating through a target site. For example, cases of complications such as peritoneal punctures accompanied with intraperitoneal organ punctures have occurred here and there in association with the growing significance for truncal blocks due to the increase in the number of patients receiving anticoagulant therapy.

Ultrasonography is often utilized in vascular puncture as well, for example, in emergency situations such as in emergency outpatient service. In such situations, patients can be in critical conditions due to bleeding or the like and thus, in general, even an operator who is highly skilled in vascular puncture, such as an anesthesiologist, would utilize ultrasonography to perform vascular puncture for safety's sake. In emergency cases, however, such operator with excellent technical skill may not be always available; consequently, even when ultrasonography is utilized in order to confirm the target blood vessel, operational mistakes can still occur.

CITATION LIST

Non Patent Literatures

Non Patent Literature 1: A Shido, The Journal of Japan Society for Clinical Anesthesia Vol. 30 No. 7, 2010.
Non Patent Literature 2: Y Fujiwara, T Komatsu, Anesthesia 21 Century Vol. 9 No. 2-28 2007.

SUMMARY OF INVENTION

Technical Problem

With the aforementioned circumstances as the background, an object of the present invention is to provide an ultrasound-guided puncture assist device that is capable of preventing occurrence of operational mistakes when a nerve block or vascular puncture is performed under ultrasonography, an ultrasound-guided puncture method using the ultrasound-guided puncture assist device, and the like.

Solution to Problem

The inventors suspected that one of the causes for occurrence of peritoneal puncture and mispuncture, excluding procedural inexperience of the operator, is narrowing of the injection target site, such as a blood vessel, fascia, or muscle (hereinafter, called "blood vessel(s) or the like" in short).

That is, when a vascular puncture is performed under ultrasonography, the target site such as a blood vessel or the like will be probed for with an ultrasound probe being pressed against the surface of the target site. Since blood vessels or the like are soft tissues, it occurred to the inventors that blood vessels or the like would become narrower compressed by a probe and that this narrowing may increase the possibility of mispuncture occurrence with needle or the like.

The inventors then studied this issue of narrowing, and confirmed that compression on the surface of a target site does result in narrowing of a blood vessel or the like. Further, the inventors found that pulling the surface of a target site can increase the width of the blood vessel or the like, providing a condition that facilitates performing puncture with needle or the like.

Based on this finding, the inventors came to a thought that, when performing a nerve block or vascular puncture, if one can maintain the pulling of the surface of a target site without impairing the compression made by a probe used in ultrasonography, the width of the blood vessel or the like can be increased, whereby mispuncturing with needle or the like can be prevented. The thought has led the inventors to a technical idea that did not exist previously, to embody the thought in the form of an ultrasound-guided puncture assist device and an ultrasound-guided puncture method using the same.

The invention includes the following configurations.

A first configuration of the invention is an ultrasound-guided puncture assist device with an object of preventing narrowing or the like of a puncture target site for a nerve block or vascular puncture under ultrasonography to thereby assist the puncture by including a pulling mechanism for pulling the surface of the puncture target site, such as skin.

A second configuration of the invention is the ultrasound-guided puncture assist device according to the first configuration, wherein the pulling mechanism includes a hollow member whose interior is a cavern, and a suction passage that can be connected to a vacuum suction device through the hollow member.

A third configuration of the invention is the ultrasound-guided puncture assist device according to the second configuration, wherein the pulling mechanism further has a puncture slot provided in the hollow member to be used in puncturing with needle or the like.

A fourth configuration of the invention is the ultrasound-guided puncture assist device according to the second or third configuration, wherein the hollow member is made of a transparent or semi-transparent material.

A fifth configuration of the invention is the ultrasound-guided puncture assist device according to the second to fourth configurations, wherein the hollow member is gradually widened toward the plane to be in contact with human body.

A sixth configuration of the invention is the ultrasound-guided puncture assist device according to the first to fifth configurations, having a grip.

A seventh configuration of the invention is the ultrasound-guided puncture assist device according to the first configuration, wherein the pulling mechanism includes a pulling needle.

An eighth configuration of the invention is the ultrasound-guided puncture assist device according to the first configuration, wherein the pulling mechanism includes an adhesion mechanism utilizing adhesion.

A ninth configuration of the invention is the ultrasound-guided puncture assist device according to the second to eighth configurations, further including a mounting mechanism that enables mounting to an ultrasound probe.

Advantageous Effects of Invention

With the present invention, it is now possible to provide an ultrasound-guided puncture assist device capable of preventing occurrence of operational mistakes or the like when a nerve block or vascular puncture is performed under ultrasonography, an ultrasound-guided puncture method using the ultrasound-guided puncture assist device, and the like. That is, the use of the ultrasound-guided puncture assist device of the invention can increase the width of the target site tissue where a nerve block or vascular puncture is performed, and thus occurrence of mispuncture is preventable.

DESCRIPTION OF EMBODIMENTS

Figure 1:
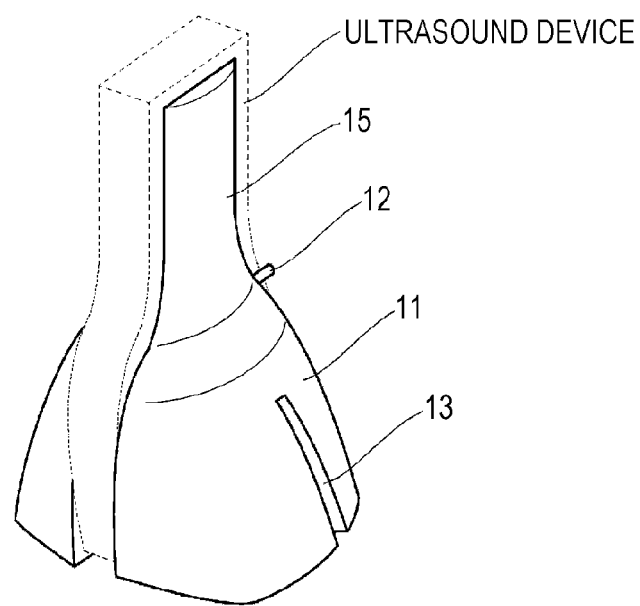
FIG. 1 is a perspective view showing an example of an ultrasound-guided puncture assist device of a vacuum suction type.

In the following, an ultrasound-guided puncture assist device (hereinafter, simply called "puncture assist device") of the invention will be described with reference to the examples in the drawings.

A pulling mechanism for pulling the surface of a puncture target site, such as skin, is a mandatory configuration in the puncture assist device of the invention. Hence, under ultrasonography, narrowing or the like of the puncture target site for a nerve block or vascular puncture can be prevented, whereby the puncturing is assisted. Not only the pulling mechanism but also other configuration(s) may be included in the puncture assist device of the invention. For example, a grip shown in FIG. 1 and a fixing mechanism that is designated as 32 in FIG. 5 can be included.

With regard to the pulling mechanism, various configurations may be employed without limitation as long as one is capable of pulling the surface of a puncture target site, such as skin. For example, a configuration in which a needle is used to hook and pull the skin surface, or a configuration in which vacuum suction or adhesion is used to stick to and pull the skin surface, can be employed.

Preferably, the pulling mechanism is of a vacuum suction type. This enables non-invasive pulling and provides the ease of adjustment of the degree of pulling, thereby having the effect of improving the handleability of the puncture assist device.

Figure 2:
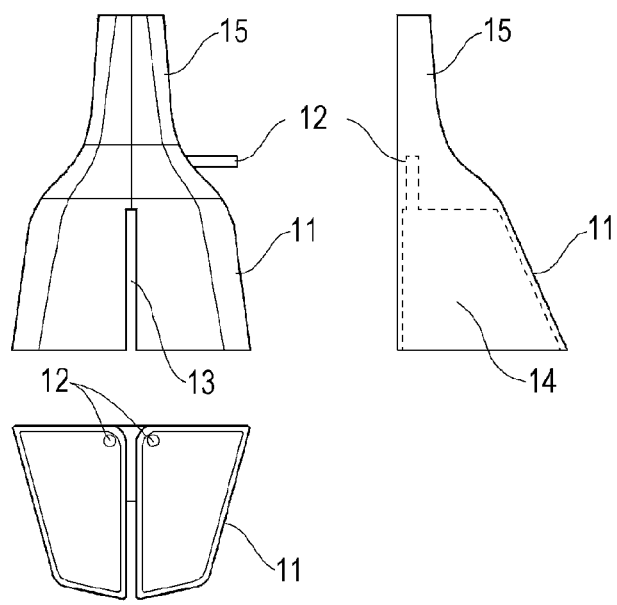
FIG. 2 is a three-orthographic view showing an example of the ultrasound-guided puncture assist device of the vacuum suction type.
Figure 3:
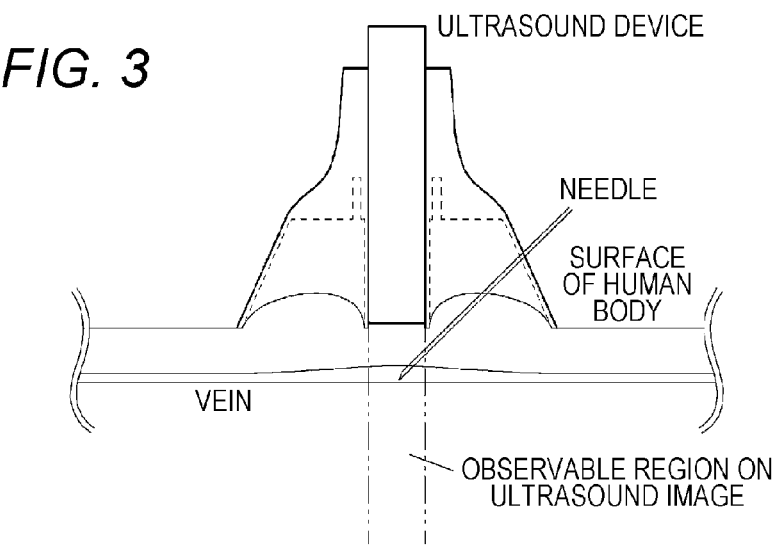
FIG. 3 is a view showing an example of how the ultrasound-guided puncture assist device of the vacuum suction type is used.

FIGS. 1 to 3 are examples of a vacuum suction-type puncture assist device 1 including a pulling mechanism utilizing vacuum suction.

A hollow member 11 and a suction passage 12 are mandatory configurations in the vacuum suction-type assist device 1. The hollow member 11 has a puncture slot 13 to be used in puncturing with needle or the like, and a cavern 14, and is provided with a grip 15 to be held in hand.

FIG. 3 will now be taken as an example to describe how to use the vacuum suction-type assist device 1.

The suction passage 12 is connected to a suction device through tubing or the like, which suction device provides vacuum suction. The hollow member 11 is then held against the surface of human body or the like to enable the pulling of the surface of human body. When the surface of human body is pulled, an underlying blood vessel such as a vein or the like is dilated, whereby it becomes easier to perform a puncture thereto. In this condition, an operator can perform the puncture with a needle through the puncture slot while checking on an ultrasound image(s), such that a vascular access or the like can be made.

With regard to the vacuum suction-type assist device, the hollow member preferably has a wide area to be in contact with human body, and for this purpose, it can adopt such a configuration that gradually widens as is shown in FIG. 1 and the like.

If the area to be in contact with human body is small, the pulling will require substantially high pressure to effect sufficient pull. This can increase the risk of causing pain and even internal hemorrhage in the pulled area. Such circumstances can be avoided by having a wide area to be in contact with human body.

The hollow member is preferably made of a transparent or semi-transparent material. This enables an operator to perform ultrasonography while checking the condition of the surface of human body, thereby having the effect of making it easier to prevent issues such as internal hemorrhage and the like. Furthermore, in a case of performing vascular puncture or the like, this enables an operator to work while checking the state of the needle tip or the like, thereby having the effect of improving success rates in vascular puncture or the like.

For such transparent or semi-transparent material(s), without limitation, silicon, polystyrenes, and the like can be used, for example.

The hollow member is preferably provided with a puncture slot. This enables puncturing with needle or the like through the puncture slot, increasing an option for puncture, thereby having the effect of improving the handleability of the puncture assist device.

The puncture slot, as shown in FIG. 1 and the like, may be provided vertically and with a width sized to allow passing of a needle. Further, the number of the puncture slot does not necessarily have to be only one, but a plurality of them may be provided.

Figure 4:
FIG. 4 is a view showing an example of an ultrasound-guided puncture assist device of a needle pull type.
Figure 5:
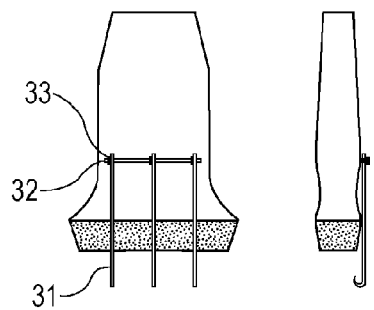
FIG. 5 is a view showing an example of the ultrasound-guided puncture assist device of the needle pull type.
Figure 6:
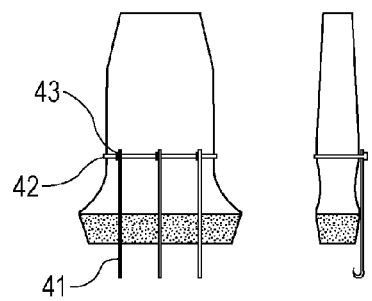
FIG. 6 is a view showing an example of the ultrasound-guided puncture assist device of the needle pull type.

The puncture assist devices shown in FIGS. 4 to 6 are examples of a puncture assist device including a pulling mechanism utilizing needle, in which a curved needle(s) at the end of the pulling mechanism is used to hook the skin surface, and then a handle is elevated or an adjustment mechanism 33 or 43 is rotated or the like so as to effect pulling.

Figure 7:
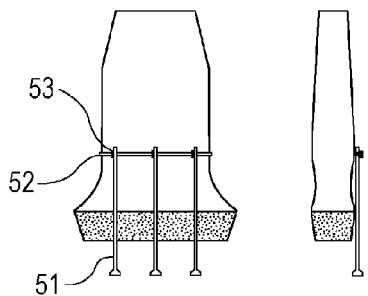
FIG. 7 is a view showing an example of an ultrasound-guided puncture assist device of an adhesion type.

The puncture assist device shown in FIG. 7 is an example of a puncture assist device including a pulling mechanism utilizing adhesion, in which an adhesive surface(s) like a suction cup(s) at the end of the pulling mechanism is adhered to the skin surface, and then an adjustment mechanism 53 is rotated or the like so as to effect pulling.

The puncture assist device of the invention can be provided with a fixing mechanism for mounting to an ultrasound probe. This enables mounting to an ultrasound probe such that an operator can handle the assist device as he operates the ultrasound probe, thereby having the effect of improving the convenience for the operator.

With regard to an ultrasound probe to be mounted, various kinds of ultrasound probe can be used without limitation as long as one is usable in vascular puncture and nerve block. Such ultrasound probes can typically include linear probes, but other probes such as convex probes, hockey stick probes, and the like can also be included.

With regard to the fixing mechanism, although there is no limitation as long as one is capable of fixing to an ultrasound probe, the fixing mechanism must be selected taking into consideration various factors of the ultrasound probe to be used, such as its shape and material properties. For example, different types of fixing means, such as a fit-in type, Velcro (registered trademark) type, adhesion type, and the like, can be selected alone or in combination as a fixing mechanism.

For example, in FIG. 1, there may be included a fixing mechanism such as Velcro (registered trademark) being wrapped around the grip 15 (not shown). Furthermore, the fixing mechanism 32 shown in FIG. 5 and the fixing mechanism 52 shown in FIG. 7 are examples of an adhesion-type fixing mechanism, in which a bar-like fixing mechanism is adhesively fixed to a linear probe. Furthermore, the fixing mechanism 42 shown in FIG. 6 is an example of a fit-in-type fixing mechanism, in which a rectangular fixing mechanism is fit into a linear probe, thereby fixed thereto.

The ultrasound-guided puncture method, in which puncture with needle or the like for nerve block or vascular puncture is performed using the ultrasound-guided puncture assist device of the invention, enables prevention of narrowing of a target puncture site and further, increase in the width of the target puncture site, to thereby prevent occurrence of mispuncture.

Furthermore, the similar effect can be obtained by using an ultrasound probe that is equipped with the ultrasound-guided puncture assist device of the invention.

EXAMPLES

<<Measurement Examples>>

Figure 8:
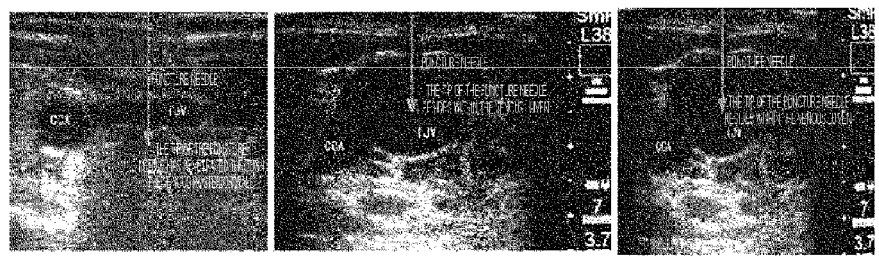
FIG. 8 shows venous comparison of when pulling and compression are applied.

1. FIG. 8 shows examples of the images from ultrasonography.
2. The image on the left in FIG. 8 was taken under normal ultrasound probe compression without pulling. It can be seen that compression by the ultrasound probe easily collapses and narrows a vein.
3. The image in the middle in FIG. 8 was taken when care was taken not to collapse the vein without pulling. In this case, applying the probe gently, lowering the patient's head by tilting the bed, setting the ventilator to a "breath holding" status so as to dilate the vein, and/or the like enables the vein to be kept from narrowing. As a result, it can be seen that the vein has an increased width compared with that under compression by the ultrasound probe.
4. The image on the right in FIG. 8 was taken when pulling was applied. As can be seen, by applying the ultrasound probe with the skin surface being pulled vertically, the lumen structure is maintained and the distance along the puncture direction is increased as compared with the image in the middle.

Experiment Example 1

<Experimental Method>

Figure 9:
FIG. 9 is a view showing a hunk of beef used in an experiment example.
Figure 10:
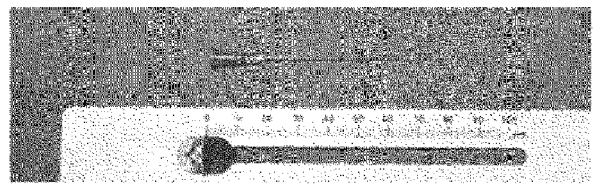
FIG. 10 shows a tool to be used as a pulling needle.
Figure 11:
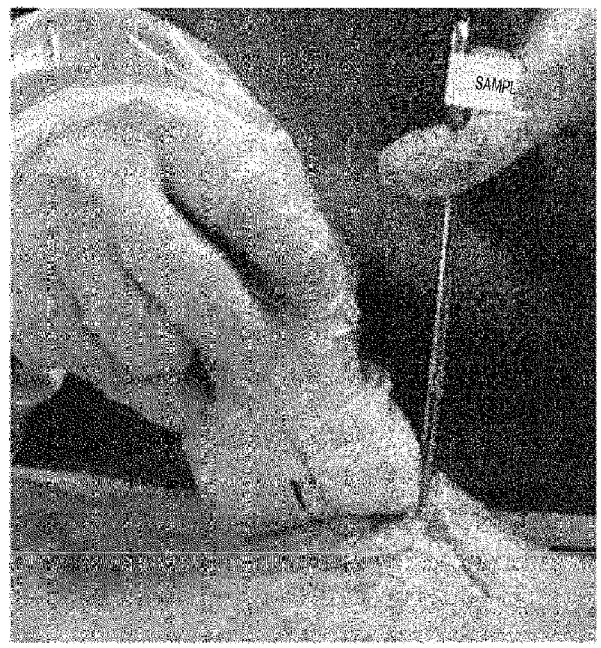
FIG. 11 is a view showing the way ultrasonography is performed as pulling is applied.
Figure 12:
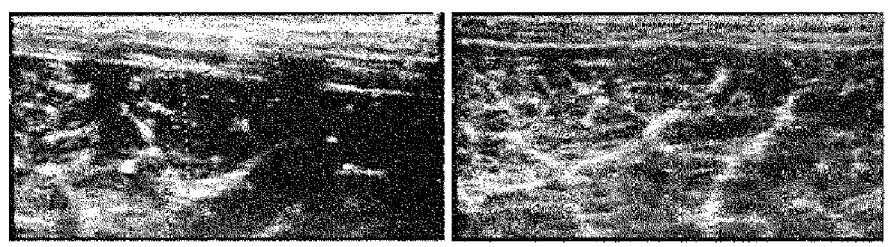
FIG. 12 shows fascial comparison of when pulling and compression are applied.

1. A commercially available, frozen hunk of beef (FIG. 9) was purchased as a measurement subject and was thawed to a room temperature of 25° C. for use.
2. Seven points were arbitrarily selected on the surface of the hunk of beef having fascia, and an ultrasound probe was made into contact therewith, around which a long injection needle whose tip had been curved was inserted into the fascia and pulled vertically (FIGS. 10 and 11).
3. In this pulling condition, a structure of muscle fiber at an arbitrary depth was selected, and the depth from the muscle surface to the structure was measured, which was designated as pulling depth (FIG. 12; on the left).
4. Next, as the muscle fiber structure was being visually observed on the ultrasound image, the pulling was released while the compression by the probe was maintained.
5. In this compression condition, the depth from the muscle surface to the structure was measured again, which was designated as compression depth (FIG. 9; on the right).
6. The measurement was performed at the arbitrary seven points; at each point the compression depth was subtracted from the pulling depth to determine the difference, and those points having the maximum and minimum difference values were excluded, while the measurement values of the remaining five points were used for statistical analysis. For the statistical analysis, a paired Wilcoxon signed-rank test was used.

<Experimental Results>

1. Table 1 shows the results.
2. The differences between the pulling depths and the respective compression depths at the five points had a mean: 7.46 mm; median: 7.2 mm; standard deviation: 0.93; maximum value: 8.8 mm; and minimum value: 6.6 mm, which were highly statistically significant ($P<0.01$).
3. The results indicate that utilizing the pulling and truncal block in combination may improve the level of safety in the block.

TABLE 1

|  | Measurement point 1 | Measurement point 2 | Measurement point 3 | Measurement point 4 | Measurement point 5 | Mean |
|---|---|---|---|---|---|---|
| Distance from the surface to the measured spot in the pulling condition (A; cm) | 2.050 | 1.430 | 2.180 | 1.790 | 1.450 | 1.780 |
| Distance from the surface to the measured spot in the compression condition (B; cm) | 1.170 | 0.710 | 1.510 | 0.990 | 0.790 | 1.034 |
| Difference (A minus B) | 0.880 | 0.720 | 0.670 | 0.800 | 0.660 | 0.746 |

Experiment Example 2

<Experimental Method>

Similar to Experiment Example 1, the degree of vascular dilation was measured in the subjects who were patients who received conduction anesthesia and central venous puncture. It should be noted that, patients who did not consent to the experiment or patients whose attending physician considered inappropriate were excluded from the experiment.

<Experimental Results>

1. Table 2 shows the results.

2. In all cases, the widths of the blood vessels were greater when under vacuum suction.

3. The results strongly indicate that, by performing ultrasonography utilizing vacuum suction, the width of a blood vessel is increased, facilitating vascular puncture or the like.

TABLE 2

|  | Case 1 | Case 2 | Case 3 |
|---|---|---|---|
| Width of blood vessel in the normal condition (C; mm) | 11.88 | 7.90 | 8.24 |
| Width of blood vessel in the vacuum suction condition (D; mm) | 13.70 | 12.00 | 9.42 |
| Difference (D minus C) | −1.82 | −4.10 | −1.18 |

The invention claimed is:

1. An ultrasound-guided puncture assist device for assisting a puncture by preventing narrowing of a puncture target site and by dilating the puncture target site, the ultrasound-guided puncture assist device comprising:
   a pulling mechanism for pulling a surface of the puncture target site by vacuum suction; and
   a mounting mechanism that enables mounting of the ultrasound-guided puncture assist device to an ultrasound probe, wherein
   the pulling mechanism comprises:
   a hollow member made of a transparent or semi-transparent material so as to observe the surface of the puncture target site through the hollow member, an interior of the hollow member being a cavern;
   a suction passage connecting to the hollow member, the suction passage capable of being connected to a vacuum suction device, and
   a puncture slot provided in the hollow member for puncturing with a needle.

2. The ultrasound-guided puncture assist device according to claim 1, wherein the hollow member is widened toward a plane to be in contact with the surface of the puncture target site.

3. The ultrasound-guided puncture assist device according to claim 1, having a grip.

* * * * *